United States Patent
Suda et al.

(10) Patent No.: US 6,673,312 B2
(45) Date of Patent: Jan. 6, 2004

(54) STERILIZING METHOD BY FAR-INFRARED RADIATION

(75) Inventors: Yoshihisa Suda, Tokyo (JP); Noboru Kanba, Tokyo (JP); Osamu Shimizu, Tokyo (JP); Mitsuru Uchiyama, Funabashi (JP)

(73) Assignee: Mitsubishi Pencil Co., Ltd., Tokyo (JP)

( * ) Notice: Subject to any disclaimer, the term of this patent is extended or adjusted under 35 U.S.C. 154(b) by 270 days.

(21) Appl. No.: 09/975,506

(22) Filed: Oct. 12, 2001

(65) Prior Publication Data

US 2002/0085946 A1 Jul. 4, 2002

(30) Foreign Application Priority Data

Oct. 13, 2000 (JP) ........................................ 2000-313863
Nov. 7, 2000 (JP) ........................................ 2000-339579

(51) Int. Cl.$^7$ ............................... A61L 2/07; A61L 2/08
(52) U.S. Cl. ........................................................ 422/22
(58) Field of Search ........................................... 422/22

(56) References Cited

U.S. PATENT DOCUMENTS 5,889,074 A * 3/1999 Hashimoto et al. ........... 522/84

FOREIGN PATENT DOCUMENTS

| JP | 4-364853 | 12/1992 |
| JP | 7-308369 | 11/1995 |
| JP | 2000-51324 | 2/2000 |

\* cited by examiner

*Primary Examiner*—Hoa Van Le
(74) *Attorney, Agent, or Firm*—Foley & Lardner

(57) ABSTRACT

A method for simplified sterilization is provided which does not use a harmful medium such as a disinfectant and ultraviolet radiation and which is able to reach all portions of objects to be sterilized, where sterilization is realized without high temperatures being generated. After applying a small amount of water or mixture of water and ethanol to an object to be sterilized, or after spraying a liquid gas, far-infrared radiation is applied using a carbon lamp which has high far-infrared radiation efficiency.

5 Claims, 2 Drawing Sheets

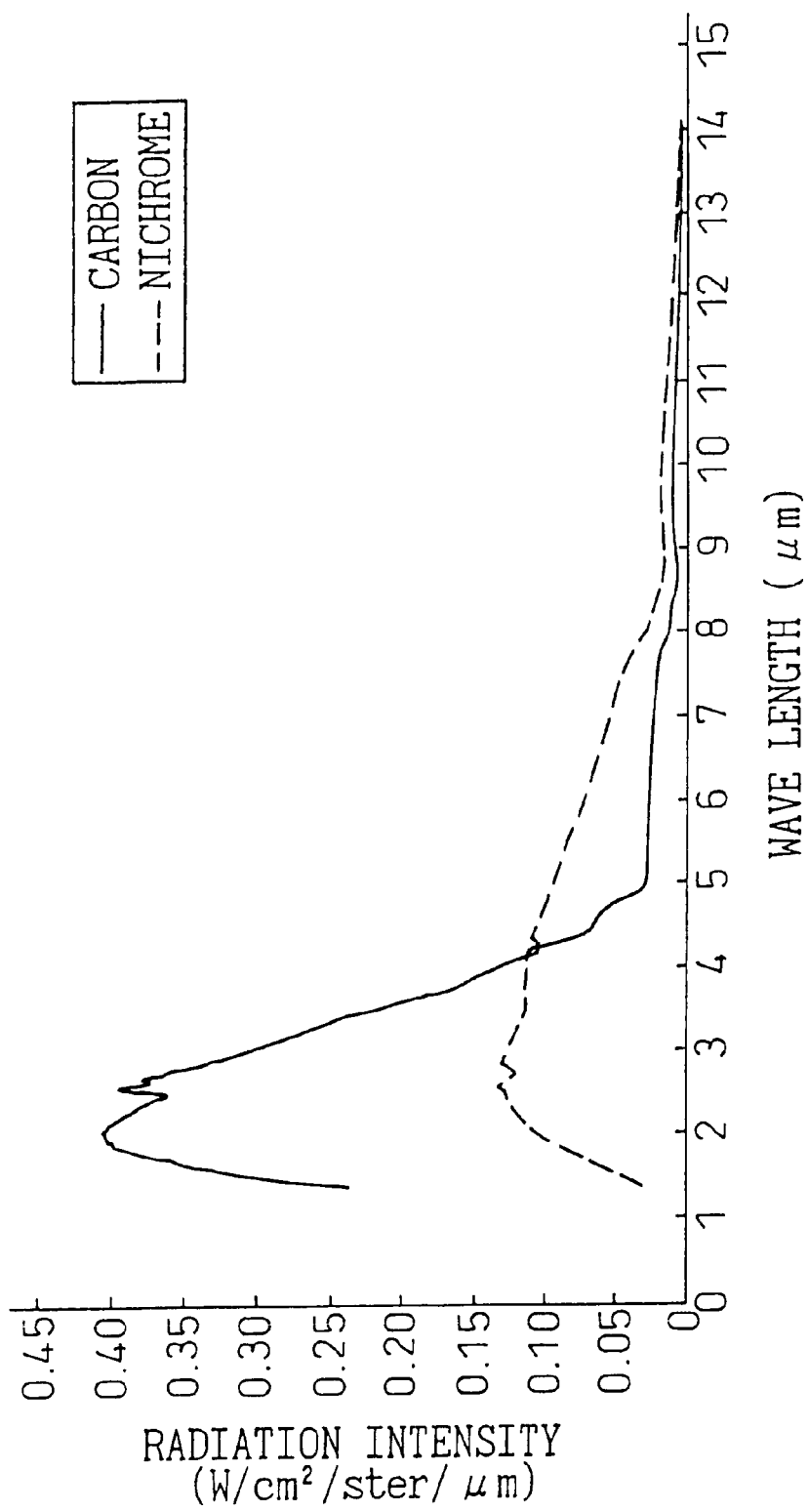

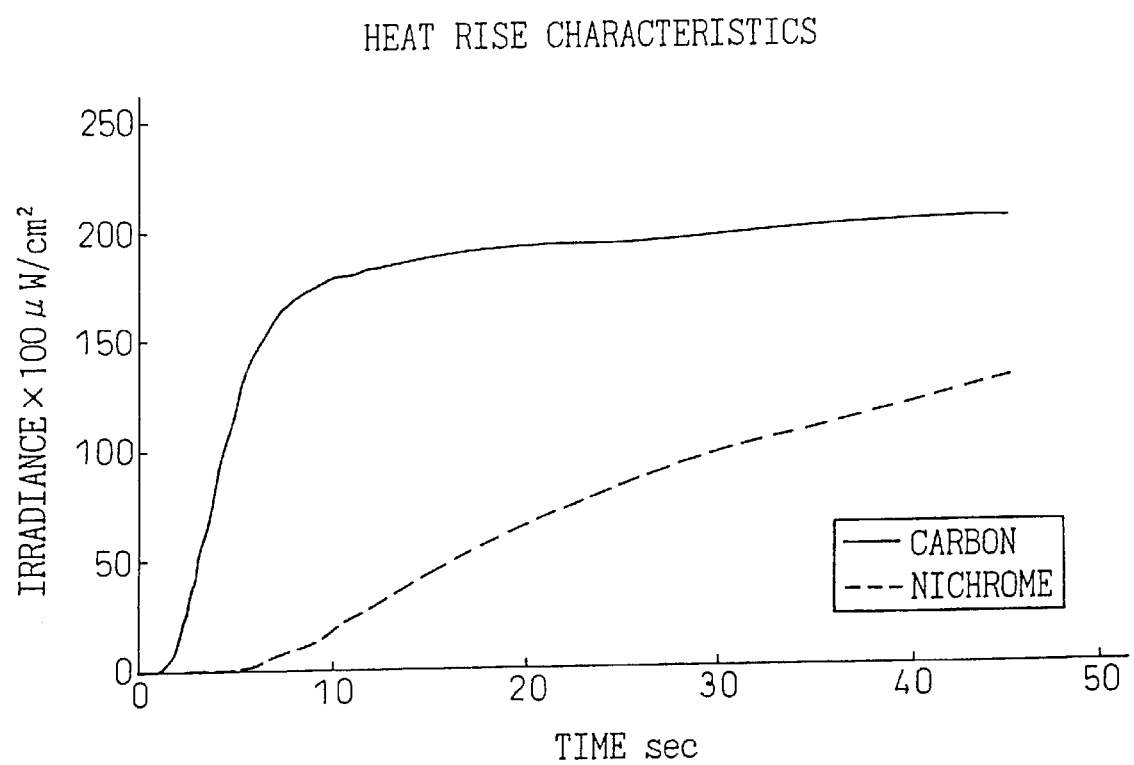

STERILIZING METHOD BY FAR-INFRARED RADIATION

BACKGROUND OF THE INVENTION

1. Field of the Invention

The present invention relates to a method for sterilization of bacteria, microorganisms and the like.

2. Description of the Related Art

According to conventional methods of sterilization, objects to be sterilized are coated with a disinfectant or irradiated with ultraviolet rays when such objects cannot be heated to a high temperature.

Various methods for sterilization using far-infrared rays have been proposed. For example, food that absorbs these rays can be sterilized by irradiation of the rays. However, such methods do no more than heat the substance itself, such as food in which the bacteria are present or adhering, to a high temperature to kill the bacteria.

Among conventional sterilization methods, methods of heating to a high temperature damage the object such as human skin, tools or the like, while it is inconvenient to use a disinfectant because of the difficulty in achieving complete sterilization, because of the generation of bacteria resistant to the disinfectant, and because of its own harmful effects and odor. Methods of using ultraviolet radiation have drawbacks in that portions which are not irradiated are not sterilized and continuous radiation deteriorates the object.

Kokai (Jpn. Unexamined Patent Publication) 4-364853 discloses a method for sterilization by heating after a liquid is adhered to objects to be sterilized. The sterilization is effected by high temperature heating and the absorption characteristics of far-infrared rays are not taken into consideration.

Kokai (Jpn. Unexamined Patent Publication) 7-308369 teaches a sterilization technology of radiating far-infrared rays to objects to be sterilized after applying water having high far-infrared ray absorption. However, a large scale structure is needed to practice the invention, because it is necessary to use a device made specially for applying to the objects water having high far-infrared ray absorption. In addition, it is difficult to place body portions other than the fingers into the device. Because a far-infrared heater of a conventional ceramic type is used as a far-infrared radiation source, much time is needed to raise and lower the temperature of the heater. Therefore, the heater should always be active, thus consuming considerable energy, and is accordingly impractical. Although an infrared ray lamp and a halogen heater of which on-off change is carried out easily are used, their sterilization efficiency is extremely poor, because their far-infrared radiation efficiency is markedly inferior to that of a far-infrared heater. In addition, directly applied water leads to breeding of bacteria because of insufficient removal of residual water.

SUMMARY OF THE INVENTION

The first object of the invention is, therefore, to provide a simplified sterilization method not using a harmful medium such as a disinfectant or ultraviolet rays, and to provide a method using a means for effectively radiating far-infrared rays, whereby a simplified sterilization process can be performed on all desired portions of objects which cannot be heated to a high temperature.

The second object of the present invention is to provide a method which enables sterilization without directly supplying water to the objects.

According to the invention, there is provided a first method of sterilization, comprising applying water having high absorption of far-infrared rays or a liquid mixture of the water and ethanol to objects to be sterilized, and radiating far-infrared rays by use of a small carbon lamp which is highly efficient in radiating the rays, whereby objects are effectively sterilized.

According to the invention there is provided a second method of sterilization, comprising the steps of supplying a wet air or a saturated vapor as a source of a very small quantity of moisture around an object, and then radiating far-infrared rays by use of a carbon lamp.

The wet air or saturated vapor can be generated by supplying a liquid gas or an air including the liquid gas.

As the heating source for the carbon lamp, a carbon material having high far-infrared ray radiation efficiency is used. The material is sealed preferably with an inert gas such as argon, in a container made of a heat resistant material such as quartz.

The above method of supplying a very small quantity of moisture can be applied not only to sterilization of fingers but also to sterilization in order to preserve cultural assets since excess moisture is not supplied to and around the objects. Since the very small amount of moisture supplied according to the method of the present invention evaporates during the sterilization process, the following process of removing the moisture is not needed, and in addition, breeding of bacteria caused by residual moisture can be prevented.

The carbon material having high far-infrared ray radiation efficiency is obtained by mixing an excipient composition, which has a high yield of carbon residue after being sintered, with one or more kinds of carbon powder such as carbon black, graphite and coke, a metallic compound such as a metallic carbide, a metallic borate, a metallic silicate, a metallic nitrate, a metallic oxide, etc., molding and sintering the mixture to provide the product with a desired resistance during the sintering and carbonizing process. The product obtained has an optional specific resistance and form. It has been confirmed that the problems mentioned above are effectively solved because it is possible to control heat generation by a predetermined current and potential and because the product has excellent in heat generating performance and efficiency, as well as far-infrared generating performance.

The preferred embodiments of the present invention are described hereinafter, but it is to be understood that the invention is not limited to the embodiments.

BRIEF DESCRIPTION OF THE DRAWINGS

FIG. 1 is a graph showing radiation characteristics of the carbon lamp of the present invention; and FIG. 2 is a graph showing heat rise characteristics of the carbon lamp of the present invention.

EXAMPLES

Example 1

As the starting material for the heat generating source of the carbon lamp having high far-infrared ray radiation efficiency, a resin mixture system was used which comprises 45 mass parts of a chlorinated vinyl chloride resin (Nippon Carbide KK(T-741) and 15 mass parts of a furan resin (Hitachi Kasei KK, HITAFURAN VF-302). In addition, 10 mass parts of fine powder of natural graphite (Nippon Kokuen KK, average particle size: 5 μm), 30 mass parts of boron nitride (Shinetsu Kagaku KK, average particle size: 2 μm) and 20 mass parts of diallyl phthalate monomer used as a plasticizer were added to the resin mixture system. The resultant mixture was dispersed, mixed and extrusion-molded. Then, the product was sintered in a nitrogen gas atmosphere to obtain a rectangular heat-generating source of a carbon type. The heat-generating source was cut to a 50 mm piece, and was provided with lead wires at its ends, placed in a quartz tube containing an argon gas atmosphere to form a small carbon lamp heater. The heater was mounted on a device provided with a reflecting plate. When the device was excited at 100V-300W, the carbon part of the device immediately reached a temperature of 1,100° C., and the outer surface of the quartz tube reached 700° C., whereby occurrence of the far-infrared radiation was confirmed. FIGS. 1 and 2 each show a comparison with a normal metallic heater source (nichrome wire) for radiation intensity characteristics and for heat rise characteristics, respectively.

A sterilization treatment was then carried out using the carbon lamp heater having the above characteristics. Coliform bacteria and staphylococcus aureus bacteria adjusted in a phosphoric buffer solution were applied to a surface of a hand which was sufficiently sterilized, washed and dried to remove moisture at room temperature. A small amount of water containing a small amount of ethanol was sprayed onto the surface. Then the far-infrared ray device was switched on to radiate rays onto the surface from a position a predetermined distance (100 mm) away. After irradiation lasting from 5 to 30 seconds, the far-infrared ray device was switched off. Immediately thereafter, the portion to which was bacteria had been applied transferred to an agar-agar medium, which was cultured for 48 hours to determine the sterilization effect. As a result, it was confirmed that sterilization effects could be obtained by way of a short-duration irradiation period of 15 seconds or longer from switch-on, as can be seen from Table 1. This shows that the far-infrared rays are absorbed into water immediately after being radiated, and is used as energy for killing the bacteria because of the excellent temperature-rise and lowering-characteristics and in the superior radiation efficiency of a carbon lamp heater over conventional far-infrared lamps. In this connection, no significant rise in temperature of the hand skin surface was observed and no skin burning occurred even after a 30-second irradiation period.

TABLE 1

Sterilization Test results

| Bacteria | Radiation Time (sec) | | | | | | |
|---|---|---|---|---|---|---|---|
| | 0 | 5 | 10 | 15 | 20 | 25 | 30 |
| Coliform | X | Δ | ○ | ○ | ○ | ○ | ○ |
| Staphylococcus Aureus | X | X | Δ | ○ | ○ | ○ | ○ |
| | | Δ | ○ | | | | |

○: Sterilization Effective
Δ: Sterilization Unclear
X: No Sterilization Effect

From the above results, it is clear that a simple and effective sterilization treatment can be realized by the far-infrared radiation method of the present invention.

Example 2

Instead of spraying a water, a liquid gas was sprayed to thereby make the surrounding air reach the dew point to supply a surface of a hand with a very small quantity of moisture, and then sterilization treatment was carried out using the carbon lamp heater of Example 1 according to the same process as Example 1.

The same result as Example 1 was obtained. In addition, adhesion of residual moisture was not observed after irradiation of far-infrared rays.

As has been explained above, the device used can be simplified and effective sterilization is possible according to the method of sterilization using a carbon lamp heater of the present invention. This is because the carbon lamp heater used in the present invention has excellent characteristics superior to those of conventional far-infrared heaters, in excellent heat generating speed and efficiency and improved far-infrared generation efficiency. Further, because the device for carrying out the method of the invention can be obtained at low cost than the conventional far-infrared radiation heater, industrial value of the invention is high.

What is claimed is:

1. A method for sterilization by a far-infrared radiation, comprising the steps of applying a liquid to objects to be sterilized, and irradiating the objects with far-infrared rays generated by a carbon lamp.

2. A method for sterilization by a far-infrared radiation according to claim 1, wherein said carbon lamp comprises a carbon type material, as a heat generating source, sealed with an inert gas in a heat resistant container.

3. A method for sterilization by far-infrared radiation according to claim 2, wherein said carbon type material is obtained by mixing a composition which has a carbon residue yield of more than 0 after being sintered, with a metallic compound at a ratio corresponding to a desired specific resistance and by sintering the mixture.

4. A method for sterilization by far-infrared radiation according to claim 1, wherein the liquid is applied to the objects by supplying an air containing minute particles of the liquid around the objects to be sterilized.

5. A method for sterilization by far-infrared radiation according to claim 4, wherein the air containing the minute particles of the liquid is supplied around the objects by supplying a liquid gas around the objects to thereby make an air surrounding the objects reach a dew point.

* * * * *